US008852301B1

(12) United States Patent
Bootsma

(10) Patent No.: US 8,852,301 B1
(45) Date of Patent: Oct. 7, 2014

(54) COMPOSITION OF LIGNIN PELLETS AND SYSTEM FOR PRODUCING

(75) Inventor: Jason Bootsma, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 945 days.

(21) Appl. No.: 12/828,028

(22) Filed: Jun. 30, 2010

Related U.S. Application Data

(60) Provisional application No. 61/221,712, filed on Jun. 30, 2009.

(51) Int. Cl.
  *B30B 9/28* (2006.01)
  *B30B 11/00* (2006.01)
  *C10L 5/08* (2006.01)
  *C10L 5/14* (2006.01)
  *C10L 5/16* (2006.01)
  *C10L 5/36* (2006.01)

(52) U.S. Cl.
  CPC . *C10L 5/143* (2013.01); *Y02E 50/30* (2013.01)
  USPC .......... 44/578; 44/590; 44/530; 44/551; 44/553; 44/564; 44/569; 44/573; 44/577; 44/579; 44/589; 44/594; 44/636

(58) Field of Classification Search
  USPC .......... 435/99, 261, 289; 422/261; 127/37; 44/504, 590, 578, 530, 551, 553, 564, 44/569, 573, 577, 579, 589, 594, 636
  See application file for complete search history.

(56) References Cited

U.S. PATENT DOCUMENTS

| | | | |
|---|---|---|---|
| 4,281,063 A * | 7/1981 | Tsao et al. | 435/99 |
| 5,980,595 A | 11/1999 | Andrews | |
| 6,506,223 B2 | 1/2003 | White | |
| 7,487,601 B2 | 2/2009 | Carin et al. | |
| 2007/0259412 A1 | 11/2007 | Belanger et al. | |
| 2008/0064906 A1 | 3/2008 | Foody et al. | |

(Continued)

FOREIGN PATENT DOCUMENTS

| WO | 2007111605 | 10/2007 |
|---|---|---|
| WO | WO2007111605 | * 10/2007 |

OTHER PUBLICATIONS

Office Action mailed Sep. 14, 2012 for U.S. Appl. No. 12/827,948, 22 pages.

(Continued)

*Primary Examiner* — Prem C Singh
*Assistant Examiner* — Chantel Graham
(74) *Attorney, Agent, or Firm* — Kagan Binder, PLLC

(57) ABSTRACT

A system for treating biomass for the production of a composition of lignin pellets .is disclosed. Pellets comprising at least 50 percent lignin by dry weight is disclosed. Also disclosed are pellets produced from a lignin composition by a process comprising: pre-treating lignocellulosic biomass into pre-treated biomass; separating the pre-treated biomass into a first liquid component comprising sugars and a first solids component comprising cellulose and the lignin composition; hydrolysing the first solids component of the pre-treated biomass into a hydrolysed biomass comprising sugars and the lignin composition; separating the hydrolysed biomass into a second liquid component comprising sugars and a second solids component comprising the lignin composition; supplying the second solids component comprising the lignin composition to a pelleting apparatus to produce the pellets; wherein the lignocellulosic biomass comprises cellulose, hemi-cellulose and lignin. According to an aspect, at least a portion of the lignin is not sulfonated.

28 Claims, 19 Drawing Sheets

(56) References Cited

U.S. PATENT DOCUMENTS

2010/0233771 A1* 9/2010 McDonald et al. ............ 435/161
2012/0063969 A1* 3/2012 Cornish et al. ................ 422/261

OTHER PUBLICATIONS

Office Action mailed Dec. 21, 2011 for U.S. Appl. No. 12/827,948, 73 pages.

* cited by examiner

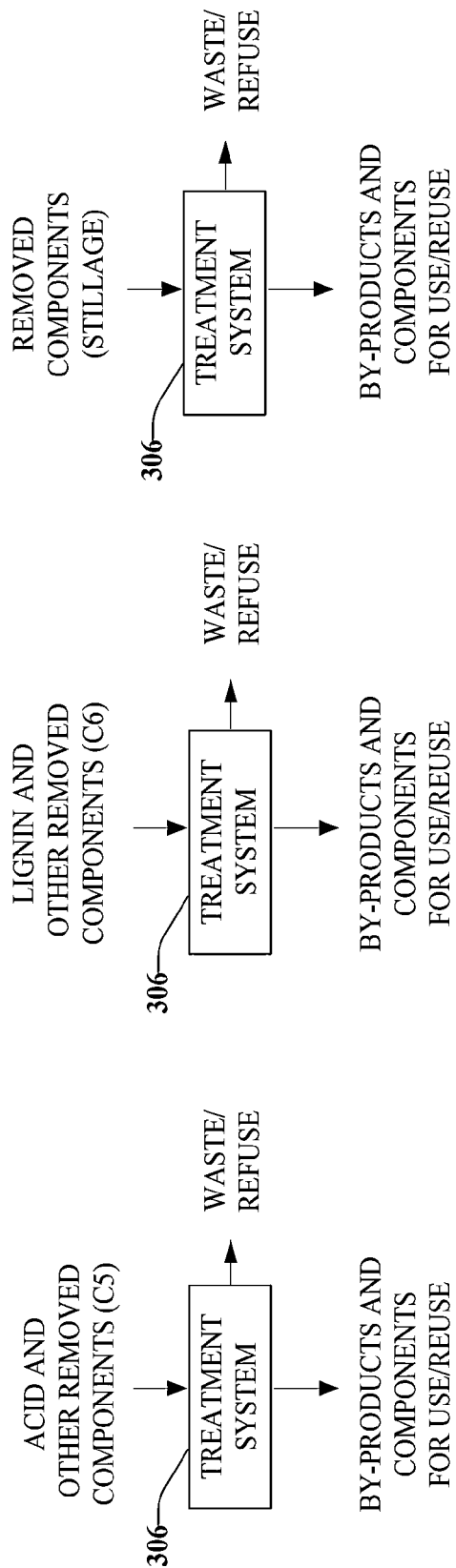

FIGURE 11A

TABLE 1A

Biomass Composition

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
| | | | | Xylan (percent) | Arabinan (percent) | Acetate (percent) | Composite (percent) | | |
| 100 | 0 | 0 | 36.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |
| 0 | 0 | 100 | 41.7 | 22.5 | 2.4 | 2.5 | 27.5 | 18.3 | 3.7 |
| 50 | 0 | 50 | 38.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 30 | 50 | 20 | 37.7 | 27.3 | 4.0 | 2.5 | 33.8 | 14.6 | 5.3 |

FIGURE 11B

TABLE 1B

Biomass Typical and Expected Composition

| | Cellulose (Glucan) (percent) (approx.) | Hemicellulose (percent) (approx.) | Lignin (percent) (approx.) | Ash (percent) (approx.) |
|---|---|---|---|---|
| Typical Range | 35-45 | 24-42 | 12-20 | 2-8 |
| Expected Range | 30-55 | 20-50 | 10-25 | 1-10 |

FIGURE 12A

TABLE 2A

Pre-Treated Biomass Liquid Component Composition

| Cob (percent) | Husks/ Leaves (percent) | Stalk (percent) | Glucose (percent) | Xylose (percent) | Arabinose (percent) | Acetic Acid (ppm) |
|---|---|---|---|---|---|---|
| 100 | 0 | 0 | 0.4 | 4.8 | 0.5 | 8090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6135 |
| 30 | 50 | 20 | 0.4 | 3.6 | 0.5 | 4763 |

FIGURE 12B
TABLE 2B

Pre-Treated Biomass
Liquid Component
Typical and Expected Composition

|  | Glucose (percent) (approx.) | Xylose (percent) (approx.) | Arabinose (percent) (approx.) | Acetic Acid (ppm) (approx.) |
|---|---|---|---|---|
| Typical Range | 0-1 | 2-6 | 0-1 | 3000-6400 |
| Expected Range | 0-1 | 1-8 | 0-1 | 2000-8000 |

FIGURE 13A
TABLE 3A

Pre-Treated Biomass
Solids Component Composition

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
|  |  |  |  | Xylan (percent) | Arabinan (percent) | Acetate (percent) | Composite (percent) |  |  |
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 3.1 |
| 50 | 0 | 50 | 55.7 | 5.5 | 0.9 | 0.6 | 13.1 | 27.0 | 2.2 |
| 50 | 50 | 0 | 57.3 | 5.4 | 0.8 | 0.5 | 10.6 | 25.2 | 5.4 |
| 30 | 50 | 20 | 55.5 | 3.8 | 0.8 | 0.6 | 11.5 | 25.4 | 5.8 |

FIGURE 13B
TABLE 3B

Pre-Treated Biomass
Solids Component
Typical and Expected Composition

|  | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 5-20 | 20-32 | 1-10 |

FIGURE 14A

TABLE 4A

Typical Composition of Lignin Component
from Hydrolysed Solids Component (C6)

|  | Cellulose (Glucan) (percent) (approx.) | Hemicellulose (percent) (approx.) | Lignin (percent) (approx.) | Ash (percent) (approx.) |
|---|---|---|---|---|
| Typical Range | 10-15 | 1.8-3.9 | 48-62 | 2-20 |

FIGURE 14B

TABLE 4B

Typical Composition of Lignin Component
from Hydrolysed and Fermented Solids Component (C6)

|  | Cellulose (Glucan) (percent) (approx.) | Hemicellulose (percent) (approx.) | Lignin (percent) (approx.) | Ash (percent) (approx.) |
|---|---|---|---|---|
| Typical Range | 5.5-7.5 | 1.8-3.9 | 57-67 | 2-22 |

FIGURE 15

TABLE 5

|  | Pellet Moisture (percent) |
|---|---|
| No Drying | 55 |
| Ambient Air 3 hours | 45 |
| Ambient Air 20 hours | 10 |
| Ambient Forced Air, 3 hours | 17 |
| Flash 3 min, Ambient Forced Air, 3 hours | 19 |
| Flash 3 min, Ambient Air 20 hours | 6.5 |
| Flash 6 min, Ambient Forced Air, 3 hours | 9 |
| Flash 6 min, Ambient Air 20 hours | 7.7 |
| Flash 12 min | 40 |

COMPOSITION OF LIGNIN PELLETS AND SYSTEM FOR PRODUCING

CROSS REFERENCE TO RELATED APPLICATIONS

The present application claims priority to and incorporates by reference U.S. Provisional Application Ser. No. 61/221,712, titled "LIGNIN TREATMENT FOR USE AS SOLID FUEL", filed on Jun. 30, 2009.

The present application relates to and incorporates by reference the following application: U.S. application Ser. No. 12/716,984, titled "SYSTEM FOR PRE-TREATMENT OF BIOMASS FOR THE PRODUCTION OF ETHANOL" filed on Mar. 3, 2010.

FIELD

The present invention relates to a system for treatment of biomass to be used in the production of ethanol. The present invention also relates to a system for producing a composition of lignin pellets.

BACKGROUND

Ethanol can be produced from grain-based feedstocks (e.g. corn, sorghum/milo, barley, wheat, soybeans, etc.), from sugar (e.g. from sugar cane, sugar beets, etc.), and from biomass (e.g. from cellulosic feedstocks such as switchgrass, corn cobs and stover, wood or other plant material).

Biomass comprises plant matter that can be suitable for direct use as a fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during or after harvesting of the corn kernels, fiber from the corn kernel, switchgrass, farm or agricultural residue, wood chips or other wood waste, and other plant matter. In order to be used or processed, biomass will be harvested and collected from the field and transported to the location where it is to be used or processed.

In a biorefinery configured to produce ethanol from biomass such as cellulosic feedstocks, ethanol is produced from lignocellulosic material (e.g. cellulose and/or hemi-cellulose). The biomass is prepared so that sugars in the cellulosic material (such as glucose from the cellulose and xylose from the hemi-cellulose) can be accessed and fermented into a fermentation product that comprises ethanol (among other things). The fermentation product is then sent to the distillation system, where the ethanol is recovered by distillation and dehydration. Other bioproducts such as lignin and organic acids may also be recovered as co-products. Lignin recovered from the cellulosic ethanol production process can be used as an energy source or as a feedstock for other chemicals or products.

Lignin is a complex mixture of aromatic compounds found in lignocellulosic biomass, such as wood, corn cobs and corn stover, switchgrass and other plant materials. Due to its high energy content, comparable to that of coal at about 8000 to 11000 BTU per pound of lignin, lignin may be used to produce renewable energy by combustion. Lignin may also be used as an additive in polymers or as a feedstock for other chemicals and products, such as adhesives, binders and carbon fibers.

It would be advantageous to provide for a pellet comprising lignin. It would also be advantageous to provide for a system for producing pellets comprising lignin. It would further be advantageous to provide for a system for producing lignin pellets from pre-treated and fermented biomass. It would further be advantageous to provide for a system that provides one or more features to facilitate improvement in the efficiency and yield of cellulosic ethanol from biomass.

SUMMARY

The present invention relates to pellets comprising lignin, wherein the pellets comprise at least 50 percent lignin by dry weight. According to an embodiment, at least a majority of the lignin is not sulfonated.

The present invention also relates to pellets produced from a lignin composition by a process comprising: pre-treating lignocellulosic biomass into pre-treated biomass; separating the pre-treated biomass into a first liquid component comprising sugars and a first solids component comprising cellulose and the lignin composition; hydrolysing the first solids component of the pre-treated biomass into a hydrolysed biomass comprising sugars and the lignin composition; separating the hydrolysed biomass into a second liquid component comprising sugars and a second solids component comprising the lignin composition; supplying the second solids component comprising the lignin composition to a pelleting apparatus to produce the pellets; wherein the lignocellulosic biomass comprises cellulose, hemi-cellulose and lignin.

DESCRIPTION OF THE DRAWINGS

FIGS. 4A, 4B and 4C are schematic block diagrams of systems for the treatment of removed components in the production of ethanol from biomass.

FIGS. 11A and 11B show TABLES 1A and 1B listing the composition of biomass comprising lignocellulosic plant material from the corn plant according to exemplary and representative embodiments.

FIGS. 12A and 12B show TABLES 2A and 2B listing the composition of the liquid component of pre-treated biomass according to exemplary and representative embodiments.

FIGS. 13A and 13B show TABLES 3A and 3B listing the composition of the solids component of pre-treated biomass according to exemplary and representative embodiments.

FIGS. 14A and 14B show TABLES 4A and 4B listing the typical composition of lignin component.

FIG. 15 shows TABLE 5 providing data obtained through the use of the treatment system according to exemplary embodiments.

DESCRIPTION OF THE EMBODIMENTS

Figure 1A:
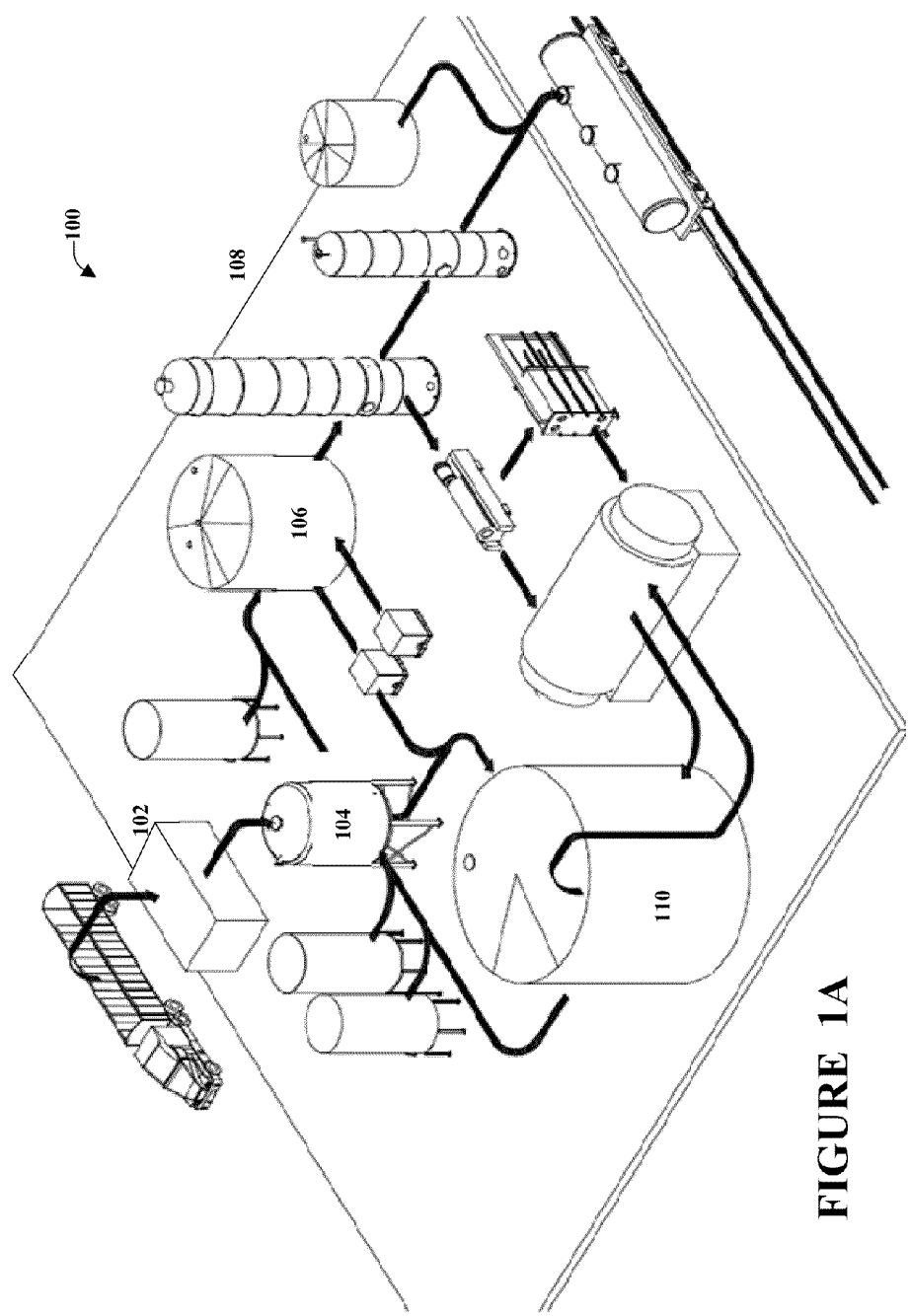
FIG. 1A is a perspective view of a biorefinery comprising a cellulosic ethanol production facility.

Referring to FIG. 1A, a biorefinery 100 configured to produce ethanol from biomass is shown.

According to an exemplary embodiment, the biorefinery 100 is configured to produce ethanol from biomass in the form of a lignocellulosic feedstock such as plant material from the corn plant (e.g. corn cobs and corn stover). Lignocellulosic feedstock such as lignocellulosic material from the corn plant comprises cellulose (from which C6 sugars such as glucose can be made available) and/or hemicellulose (from which C5 sugars such as xylose and arabinose can be made available).

As shown in FIG. 1A, the biorefinery comprises an area where biomass is delivered and prepared to be supplied to the cellulosic ethanol production facility. The cellulosic ethanol production facility comprises apparatus for preparation 102, pre-treatment 104 and treatment of the biomass into treated biomass suitable for fermentation into fermentation product in a fermentation system 106. The facility comprises a distillation system 108 in which the fermentation product is distilled and dehydrated into ethanol. As shown in FIG. 1A, the biorefinery may also comprise a waste treatment system 110 (shown as comprising an anaerobic digester and a generator). According to other alternative embodiments, the waste treatment system may comprise other equipment configured to treat, process and recover components from the cellulosic ethanol production process, such as a solid/waste fuel boiler, anaerobic digester, aerobic digester or other biochemical or chemical reactors.

Figure 1B:
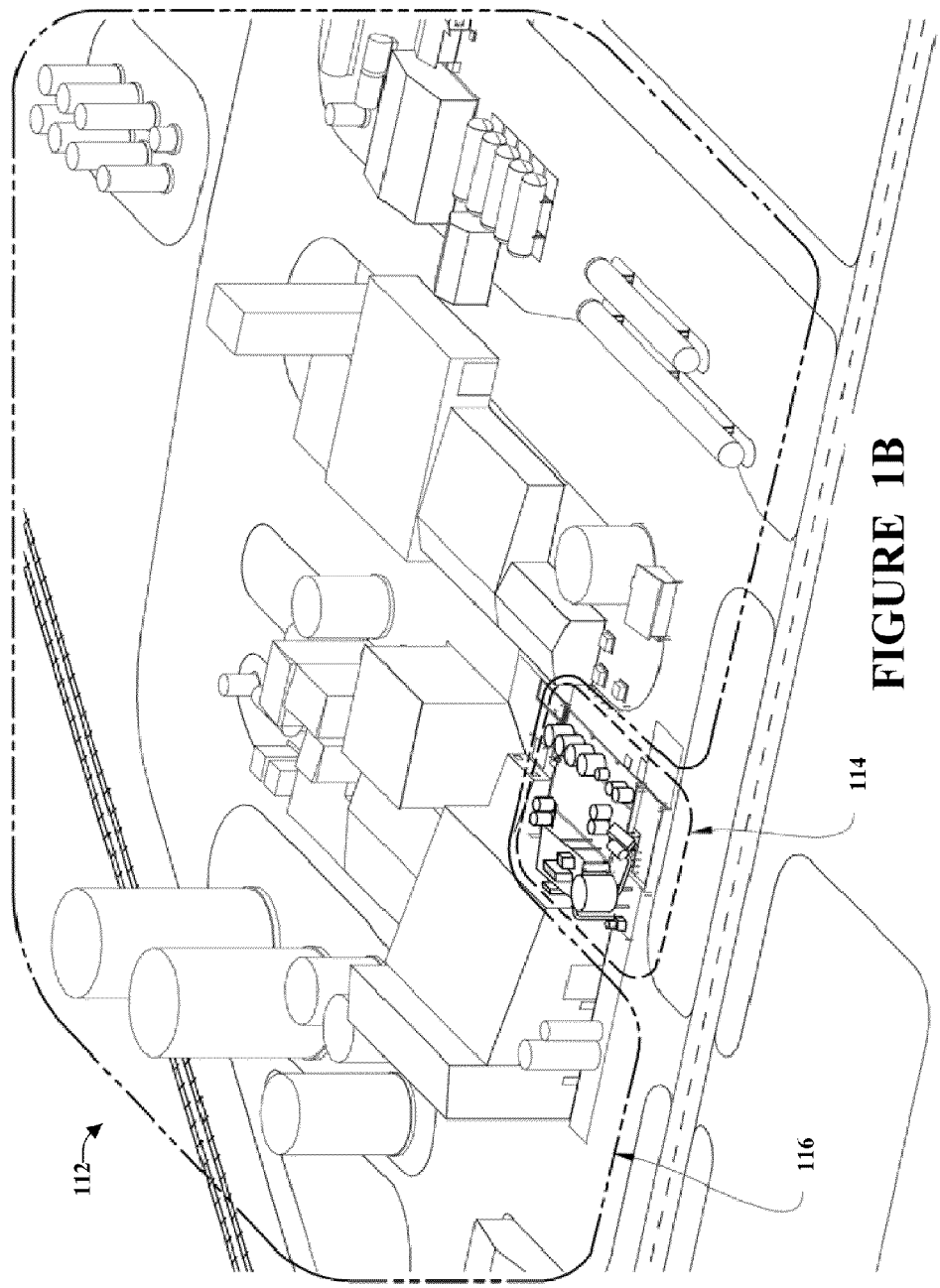
FIG. 1B is a perspective view of a biorefinery comprising a cellulosic ethanol production facility and a corn-based ethanol production facility.

As shown in FIG. 1B, according to an exemplary embodiment, a biorefinery 112 may comprise a cellulosic ethanol production facility 114 (which produces ethanol from lignocellulosic material and components of the corn plant) co-located with a corn-based ethanol production facility 116 (which produces ethanol from starch contained in the endosperm component of the corn kernel). As indicated in FIG. 1B, by co-locating the two ethanol production facilities, certain plant systems may be shared, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared for milling (e.g. by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g. a cellulosic ethanol production facility) may be co-located with other types of plants and facilities, for example an electric power plant, a waste treatment facility, a lumber mill, a paper plant or a facility that processes agricultural products.

Figure 2:
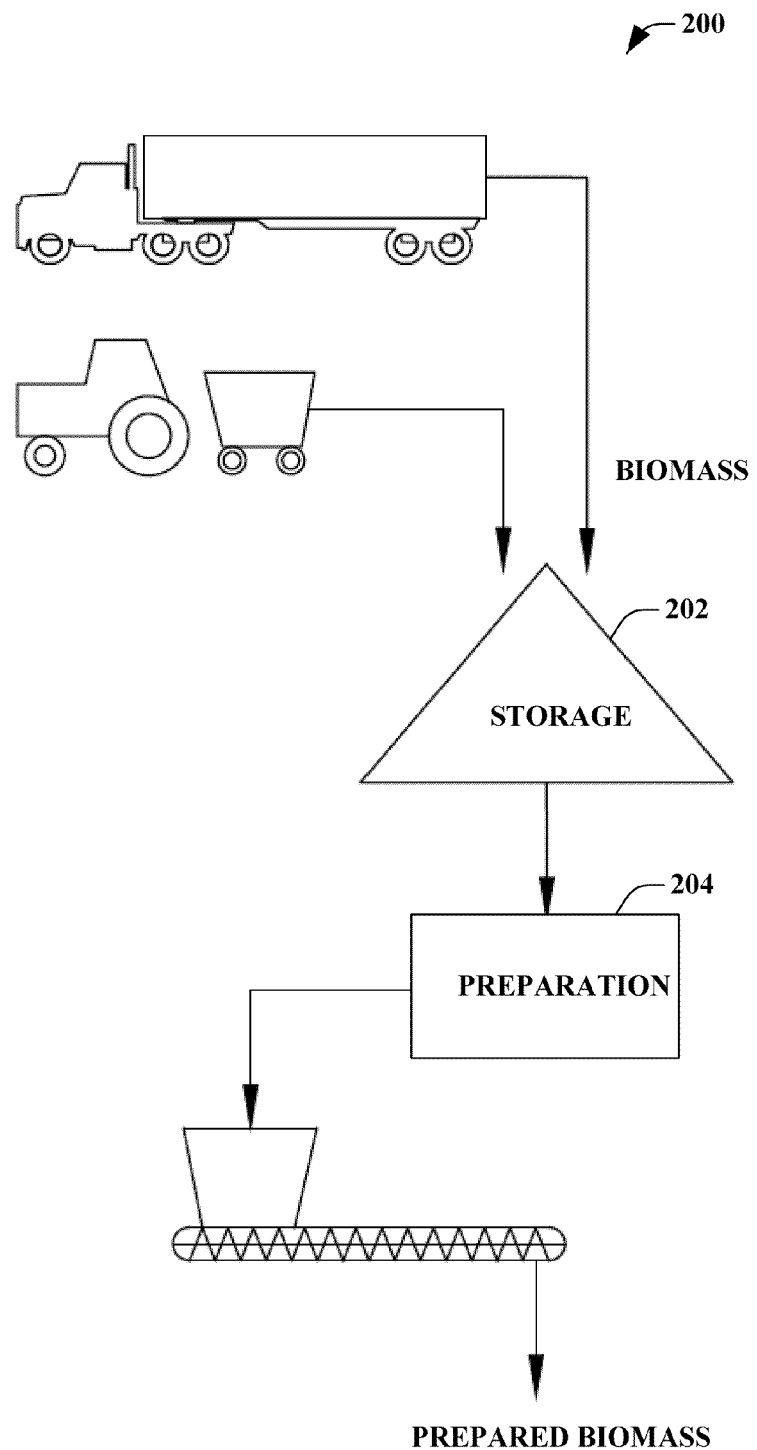
FIG. 2 is a schematic block diagram of a system for receipt and preparation of biomass for a cellulosic ethanol production facility.

Referring to FIG. 2, a system 200 for preparation of biomass delivered to the biorefinery is shown. The biomass preparation system may comprise apparatus for receipt/unloading of the biomass, cleaning (e.g. removal of foreign matter), grinding (e.g. milling, reduction or densification), and transport and conveyance for processing at the plant. According to an exemplary embodiment, biomass in the form of corn cobs and stover may be delivered to the biorefinery and stored 202 (e.g. in bales, piles or bins, etc.) and managed for use at the facility. According to a preferred embodiment, the biomass may comprise at least 20 to 30 percent corn cobs (by weight) with corn stover and other matter. According to other exemplary embodiments, the preparation system 204 of the biorefinery may be configured to prepare any of a wide variety of types of biomass (e.g. plant material) for treatment and processing into ethanol and other bioproducts at the plant.

Figure 3:
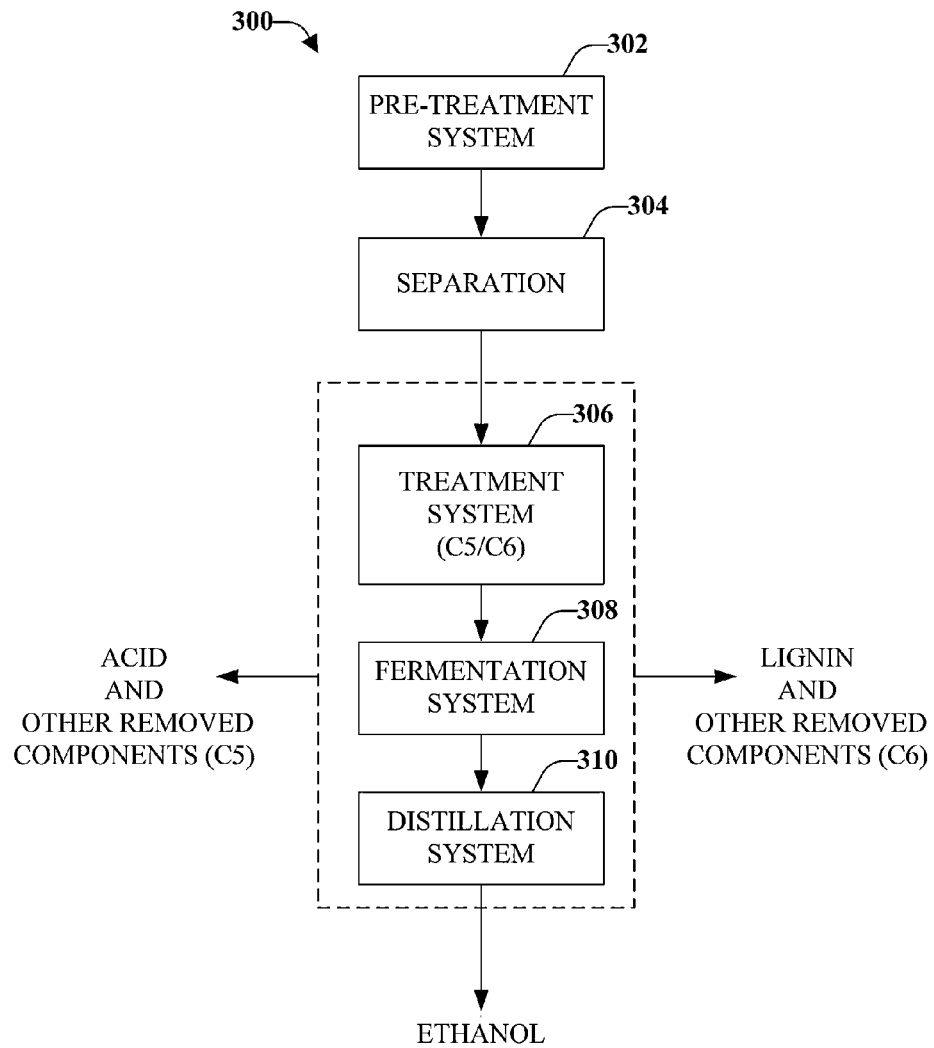
FIG. 3 is a schematic block diagram of a system for the production of ethanol from biomass.

Referring to FIG. 3, a schematic diagram of the cellulosic ethanol production facility 300 is shown. According to a preferred embodiment, biomass comprising plant material from the corn plant is prepared and cleaned at a preparation system. After preparation, the biomass is mixed with water into a slurry and is pre-treated at a pre-treatment system 302. In the pre-treatment system 302, the biomass is broken down (e.g. by hydrolysis) to facilitate separation 304 into a liquid component (e.g. a stream comprising the C5 sugars) and a solids component (e.g. a stream comprising cellulose from which the C6 sugars can be made available). The C5-sugar-containing liquid component (C5 stream) and C6-sugar-containing solids component (C6 stream) can be treated (as may be suitable) in a treatment system 306 and fermented in a fermentation system 308. Fermentation product from the fermentation system 308 is supplied to a distillation system 310 where the ethanol is recovered.

As shown in FIGS. 3 and 4A, 4B and 4C removed components from treatment of the C5 and/or C6 stream can be treated or processed to recover by-products, such as organic acids, furfural, and lignin. The removed components during treatment and production of ethanol from the biomass from either or both the C5 stream and the C6 stream (or at distillation) can be treated or processed into bioproducts or into fuel (such as lignin for a solid fuel boiler or methane produced by treatment of residual/removed matter such as acids and lignin in an anaerobic digester) or recovered for use or reuse. As shown in FIGS. 4A, 4B and 4C, components removed during treatment and production of ethanol from the biomass from either or both the C5 stream and the C6 stream (or at distillation) may be processed into bioproducts (e.g. by-products or co-products) or recovered for use or reuse. As shown in FIG. 4C, removed components from the distillation system (such as stillage or removed solids) or from the treatment of the fermentation product before distillation (e.g. removed solids and particulate matter, which may comprise residual lignin, etc.) can be treated or processed into bioproducts or fuel (e.g. methane produced in an anerobic digester).

According to a preferred embodiment, the biomass comprises plant material from the corn plant, such as corn cobs, husks and leaves and stalks (e.g. at least upper half or three-quarters portion of the stalk); the composition of the plant material (e.g. cellulose, hemicellulose and lignin) will be approximately as indicated in TABLES 1A and 1B (e.g. after at least initial preparation of the biomass, including removal of any foreign matter). According to a preferred embodiment, the plant material comprises corn cobs, husks/leaves and stalks; for example, the plant material may comprise (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any of a wide variety of other combinations of cobs, husks/leaves and stalks from the corn plant. See TABLE 1A. According to an alternative embodiment, the lignocellulosic plant material may comprise fiber from the corn kernel (e.g. in some combination with other plant material). TABLE 1B provides typical and expected ranges believed to be representative of the composition of biomass comprising lignocellulosic material from the corn plant. According to exemplary embodiments, the lignocellulosic plant material of the biomass (from the corn plant) will comprise (by weight) cellulose at about 30 to 55 percent, hemicellulose at about 20 to 50 percent, and lignin at about 10 to 25 percent; according to a particularly preferred embodiment, the lignocellulosic plant material of the biomass (e.g. cobs, husks/leaves and stalk portions from the corn plant) will comprise (by weight) cellulose at about 35 to 45 percent, hemicellulose at about 24 to 42 percent, and lignin at about 12 to 20 percent. According to a particularly preferred embodiment, pre-treatment of the biomass will yield a liquid component that comprises (by weight) xylose at no less than 1.0 percent and a solids component that comprises (by weight) cellulose (from which glucose can be made available) at no less than 45 percent.

Figure 5A:
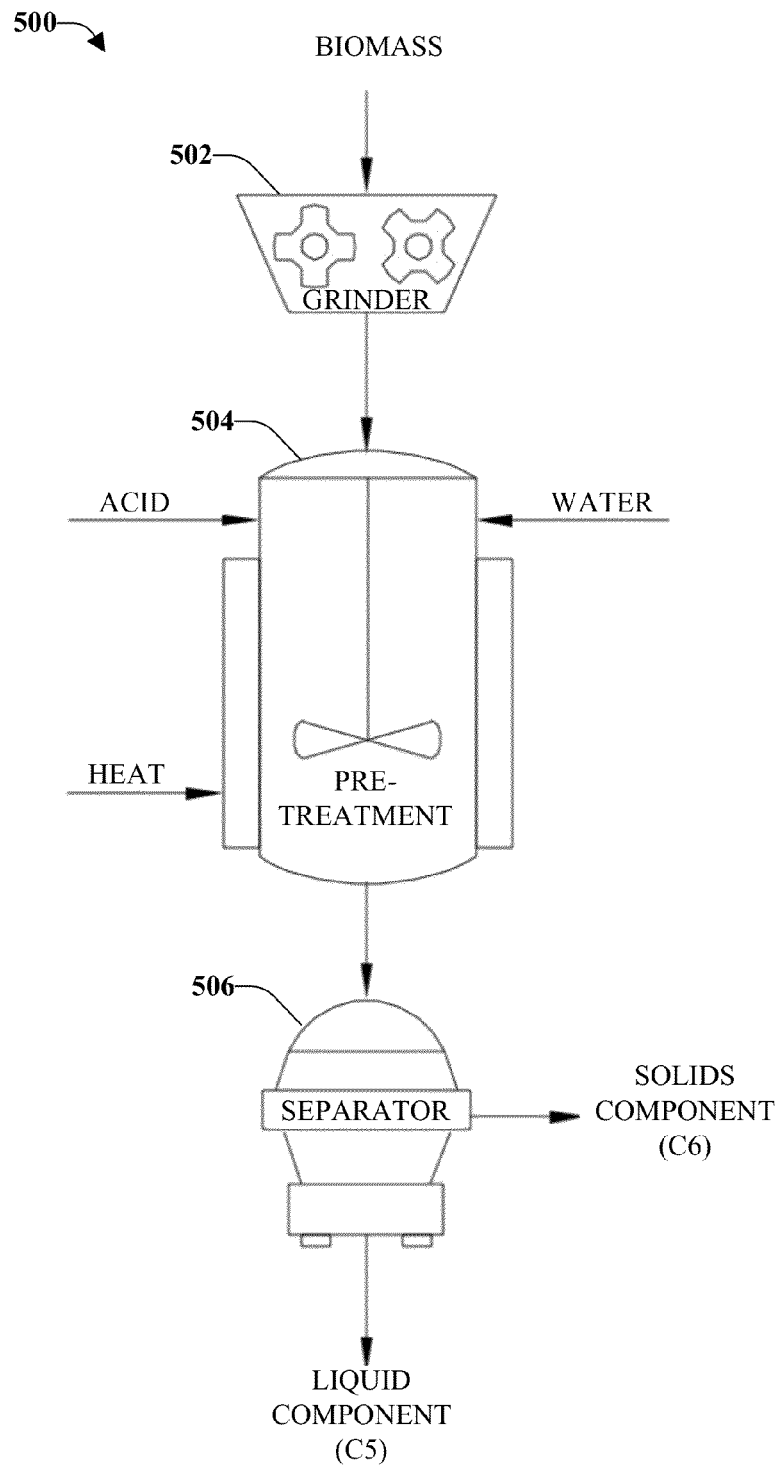
FIG. 5A is a schematic block diagram of an apparatus used for preparation, pre-treatment and separation of biomass.
Figure 5B:
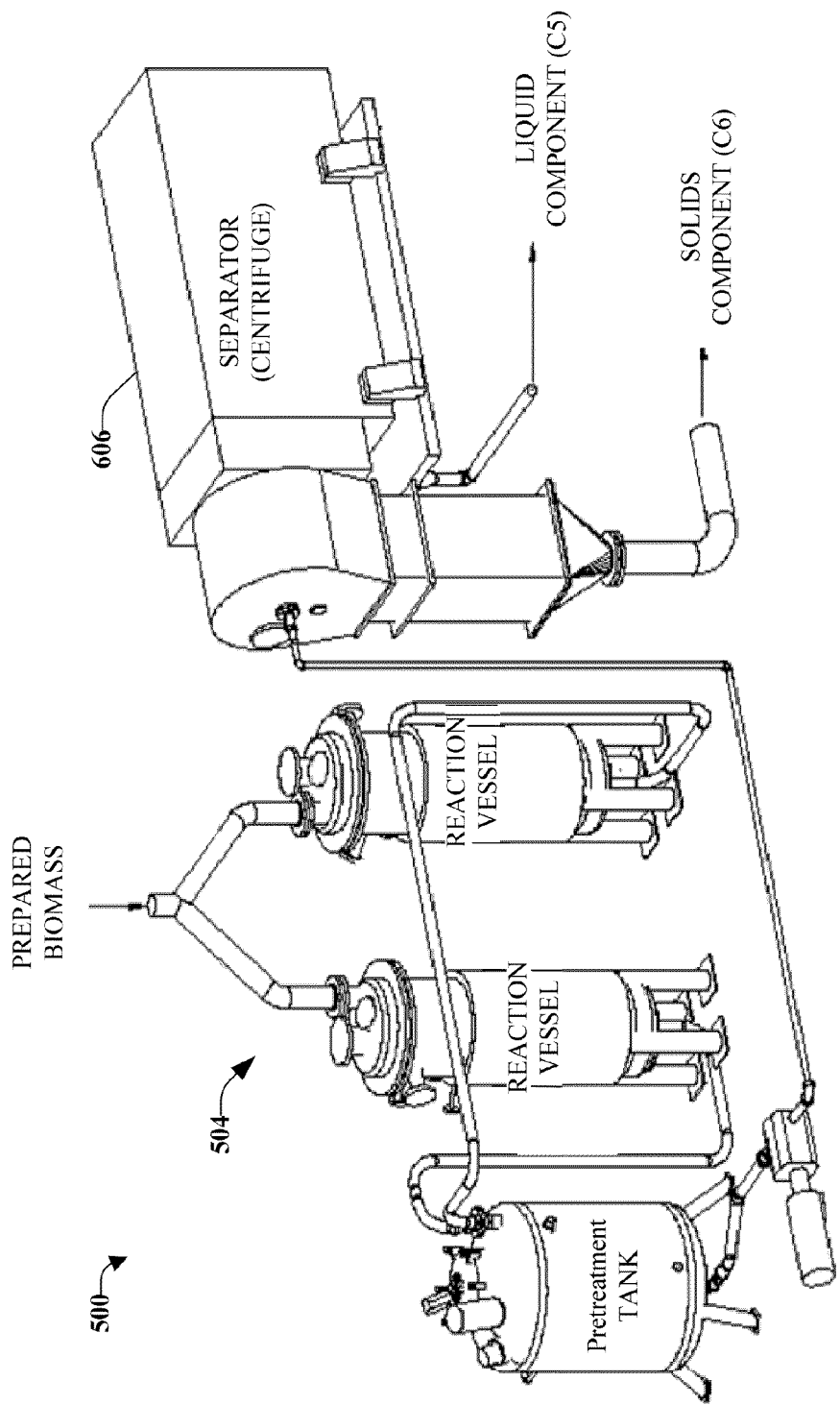
FIG. 5B is a perspective view of an apparatus used to pre-treat and separate the biomass.

FIGS. 5A and 5B show the apparatus 500 used for preparation, pre-treatment and separation of lignocellulosic biomass according to an exemplary embodiment. As shown, biomass is prepared in a grinder 502 (e.g. grinder or other suitable apparatus or mill). Pre-treatment 504 of the prepared biomass is performed in a reaction vessel (or set of reaction vessels) supplied with prepared biomass and acid/water in a predetermined concentration (or pH) and other operating conditions. As shown in FIG. 5B, the pre-treated biomass can be separated in a centrifuge 506 into a liquid component (C5 stream comprising primarily liquids with some solids) and a solids component (C6 stream comprising liquids and solids such as lignin and cellulose from which glucose can be made available by further treatment).

According to a preferred embodiment, in the pre-treatment system an acid will be applied to the prepared biomass to facilitate the breakdown of the biomass for separation into the liquid component (C5 stream from which fermentable C5 sugars can be recovered) and the solids component (C6 stream from which fermentable C6 sugars can be accessed). According to a preferred embodiment, the acid can be applied to the biomass in a reaction vessel under determined operating conditions (e.g. acid concentration, pH, temperature, time, pressure, solids loading, flow rate, supply of process water or steam, etc.) and the biomass can be agitated/mixed in the reaction vessel to facilitate the break down of the biomass. According to exemplary embodiments, an acid such as sulfuric acid, hydrochloric acid, nitric acid, phosphoric acid, acetic acid, etc. (or a formulation/mixture of acids) can be applied to the biomass. According to a particularly preferred embodiment, sulfuric acid will be applied to the biomass in pre-treatment.

The liquid component (C5 stream) comprises water, dissolved sugars (such as xylose, arabinose and glucose) to be made available for fermentation into ethanol, acids and other soluble components recovered from the hemicellulose. (TABLE 2B provides typical and expected ranges believed to be representative of the composition of biomass comprising lignocellulosic material from the corn plant.) According to an exemplary embodiment, the liquid component may comprise approximately 5 to 7 percent solids (e.g. suspended/residual solids such as partially-hydrolysed hemicellulose, cellulose and lignin). According to a particularly preferred embodiment, the liquid component will comprise at least 2 to 4 percent xylose (by weight); according to other exemplary embodiments, the liquid component will comprise no less than 1 to 2 percent xylose (by weight). TABLES 2A and 2B list the composition of the liquid component of pre-treated biomass (from prepared biomass as indicated in TABLES 1A and 1B) according to exemplary and representative embodiments.

The solids component (C6 stream) comprises water, acids and solids such as cellulose from which sugar, such as glucose, can be made available for fermentation into ethanol, and lignin. (TABLE 3B provides typical and expected ranges believed to be representative of the composition of biomass comprising lignocellulosic material from the corn plant.) According to an exemplary embodiment, the solids component may comprise approximately 10 to 40 percent solids (by weight) (after separation); according to a particularly preferred embodiment, the solids component will comprise approximately 20 to 30 percent solids (by weight). According to a preferred embodiment, the solids in the solids component comprise no less than 30 percent cellulose and the solids component may also comprise other dissolved sugars (e.g. glucose and xylose). TABLES 3A and 3B list the composition of the solids component of pre-treated biomass (from prepared biomass as indicated in TABLES 1A and 1B) according to exemplary and representative embodiments.

During pre-treatment, the severity of operating conditions (such as pH, temperature and time) may cause formation of components that are inhibitory to fermentation. For example, under some conditions, the dehydration of C5 sugars (such as xylose or arabinose) may cause the formation of furfural. Acetic acid may also be formed, for example, when acetate is released during the break down of hemicellulose in pre-treatment. Sulfuric acid, which may be added to prepared biomass to facilitate pre-treatment, if not removed or neutralized, may also be inhibitory to fermentation. According to an exemplary embodiment, by adjusting pre-treatment conditions (such as pH, temperature and time), the formation of inhibitors can be reduced or managed; according to other exemplary embodiments, components of the pre-treated biomass may be given further treatment to remove or reduce the level of inhibitors (or other undesirable matter).

Figure 6A:
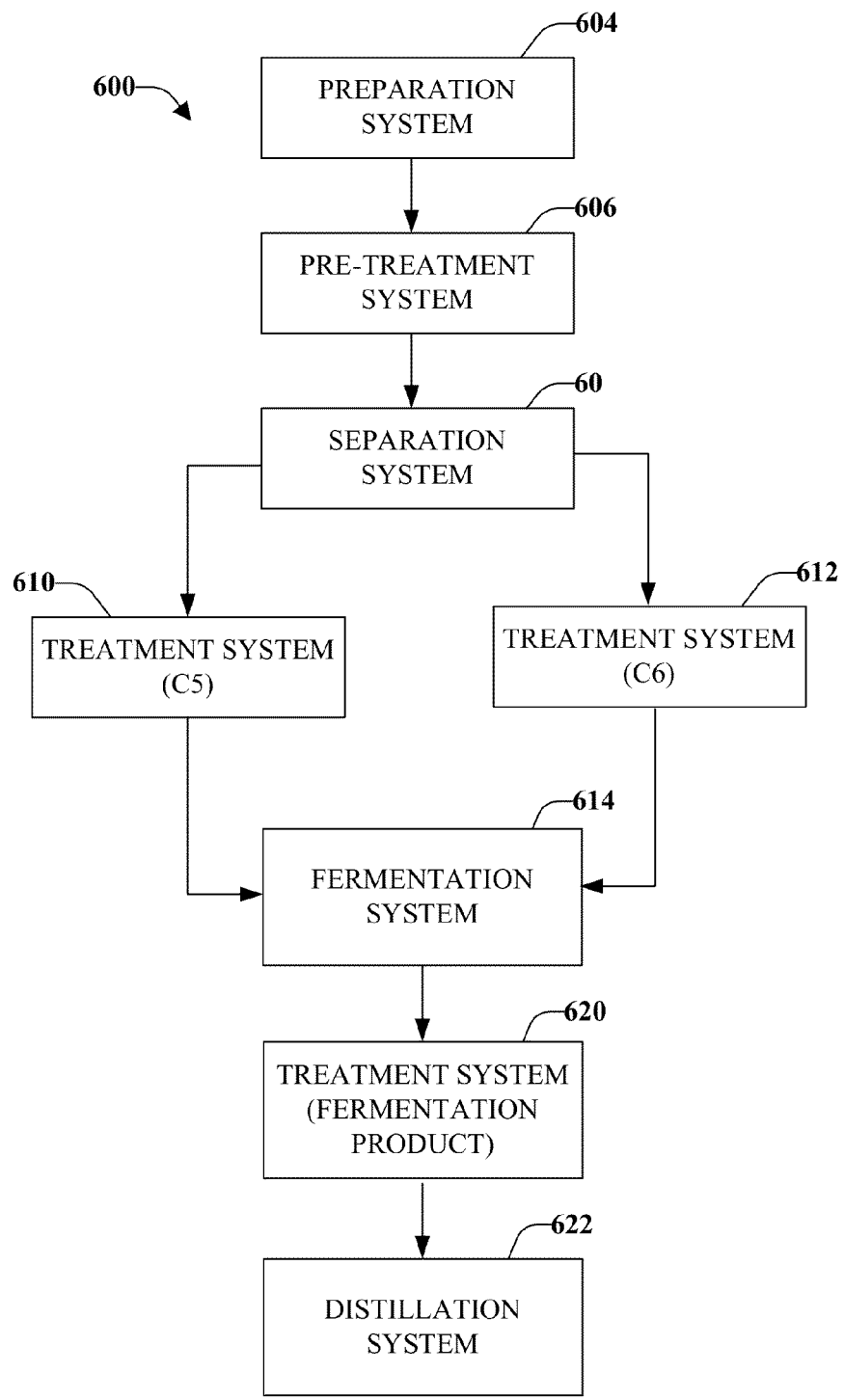
FIGS. 6A and 6B are schematic diagrams of the process flow for systems for the production of ethanol from biomass.
Figure 6B:
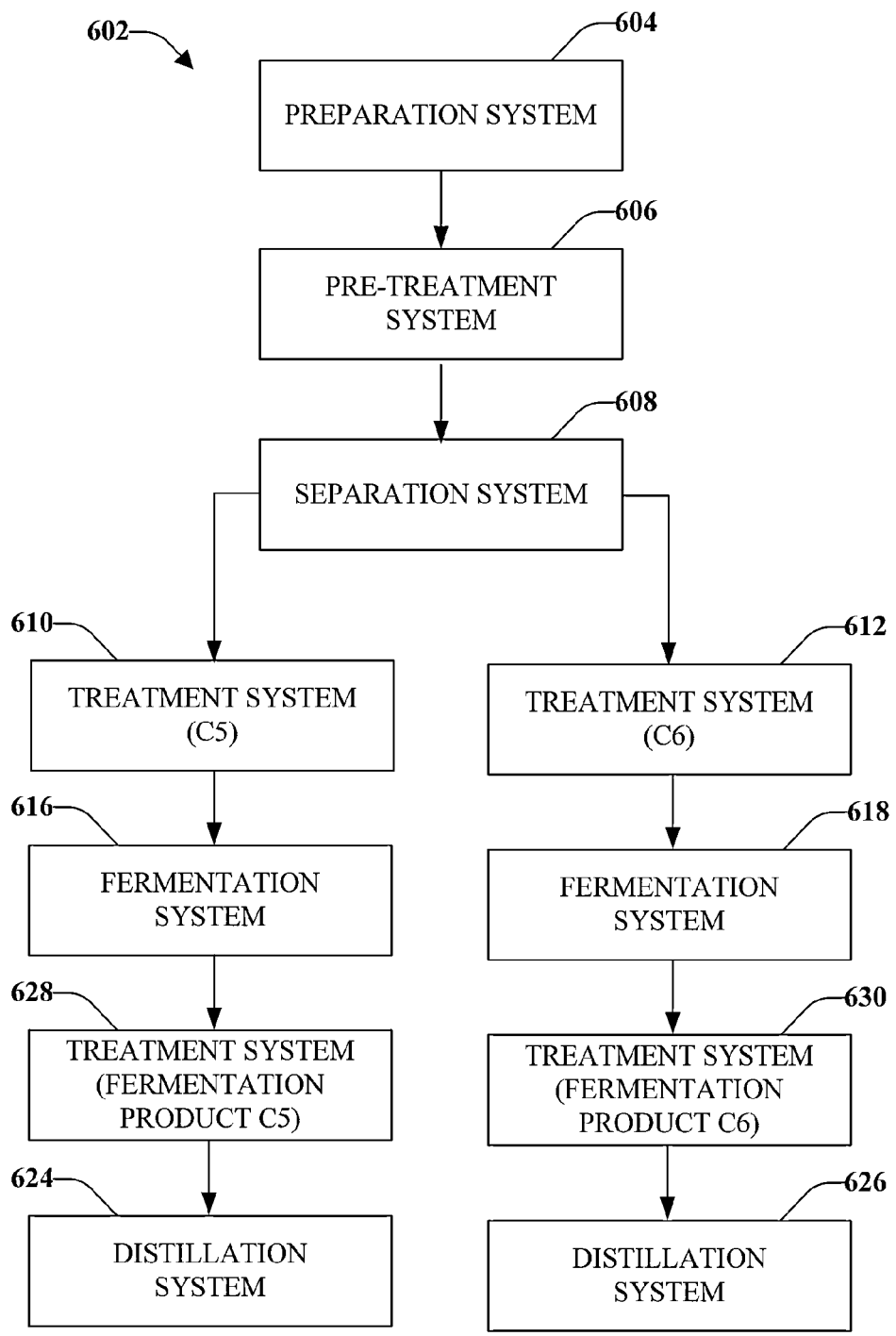

Referring to FIGS. 6A and 6B, after pre-treatment and separation the C5 stream and the C6 stream are processed separately; as shown, the C5 stream and the C6 stream may be processed separately (in separate treatment systems 610, 612) prior to co-fermentation 614 (C5/C6 fermentation as shown in FIG. 6A) or processed separately (in separate treatment systems 610, 612) including separate fermentation (separate C5 fermentation and C6 fermentation 616, 618 as shown in FIG. 6B).

Treatment of the C5 stream (liquid component) of the biomass may be performed in an effort to remove components that are inhibitory to efficient fermentation (e.g. furfural, hydroxymethylfurfural (HMF), sulfuric acid and acetic acid) and residual lignin (or other matter) that may not be fermentable from the C5 sugar component so that the sugars (e.g. xylose, arabinose, as well as other sugars such as glucose) are available for fermentation. The C5 sugars in the C5 stream may also be concentrated to improve the efficiency of fermentation (e.g. to improve the titer of ethanol for distillation).

Treatment of the C6 stream (solids component) of the biomass may be performed to make the C6 sugars available for fermentation. According to a preferred embodiment, hydrolysis (such as enzyme hydrolysis) may be performed to access the C6 sugars in the cellulose; treatment may also be performed in an effort to remove lignin and other non-fermentable components in the C6 stream (or to remove components such as residual acid or acids that may be inhibitory to efficient fermentation).

According to an exemplary embodiment shown in FIG. 6A, after pre-treatment and separation, the C5 stream and the C6 stream can be treated separately and subsequently combined after treatment (e.g. as a slurry) for co-fermentation 614 in the fermentation system to produce a C5/C6 fermentation product from the available sugars (e.g. xylose and glucose); the C5/C6 fermentation product can (after treatment 620, if any) be supplied to the distillation system 622 for recovery of the ethanol (e.g. through distillation and dehydration). According to an exemplary embodiment shown in FIG. 6B, the C5 stream and the C6 stream can each be separately processed through fermentation 616, 618 and distillation 624, 626 (after treatment 628, 630, if any) to produce ethanol. According to any preferred embodiment, a suitable fermenting organism (ethanologen) will be used in the fermentation system; the selection of an ethanologen may be based on various considerations, such as the predominant types of sugars present in the slurry. Dehydration and/or denaturing of the ethanol produced from the C5 stream and the C6 stream may be performed either separately or in combination.

Referring to FIGS. 7A, 7B, 8A and 8B, exemplary embodiments of systems to recover a lignin component are shown. The solids component (C6) is produced in the pre-treatment system 702 by separation 704 of the pre-treated biomass into the liquid component (C5) and the solids component (C6). Pre-treatment of biomass can be performed as described in U.S. application Ser. No. 12/716,984 entitled "SYSTEM FOR PRE-TREATMENT OF BIOMASS FOR THE PRODUCTION OF ETHANOL", which is incorporated by reference in its entirety. The cellulose contained in the solids component (C6) can be treated by hydrolysis 706 (e.g. enzymatic hydrolysis using an enzyme formulation that comprises cellulase) to make available the sugars (e.g. glucose) for fermentation. Enzyme hydrolysis using a cellulase enzyme formulation will generally not break down the lignin in the solids component. Lignin will comprise a substantial constituent of the residual solids in the treated solids component (e.g. hydrolysate) after enzyme hydrolysis of the cellulose. Lignin is unfermentable with the conventional ethanologen formulation used to ferment glucose into ethanol.

Figure 7A:
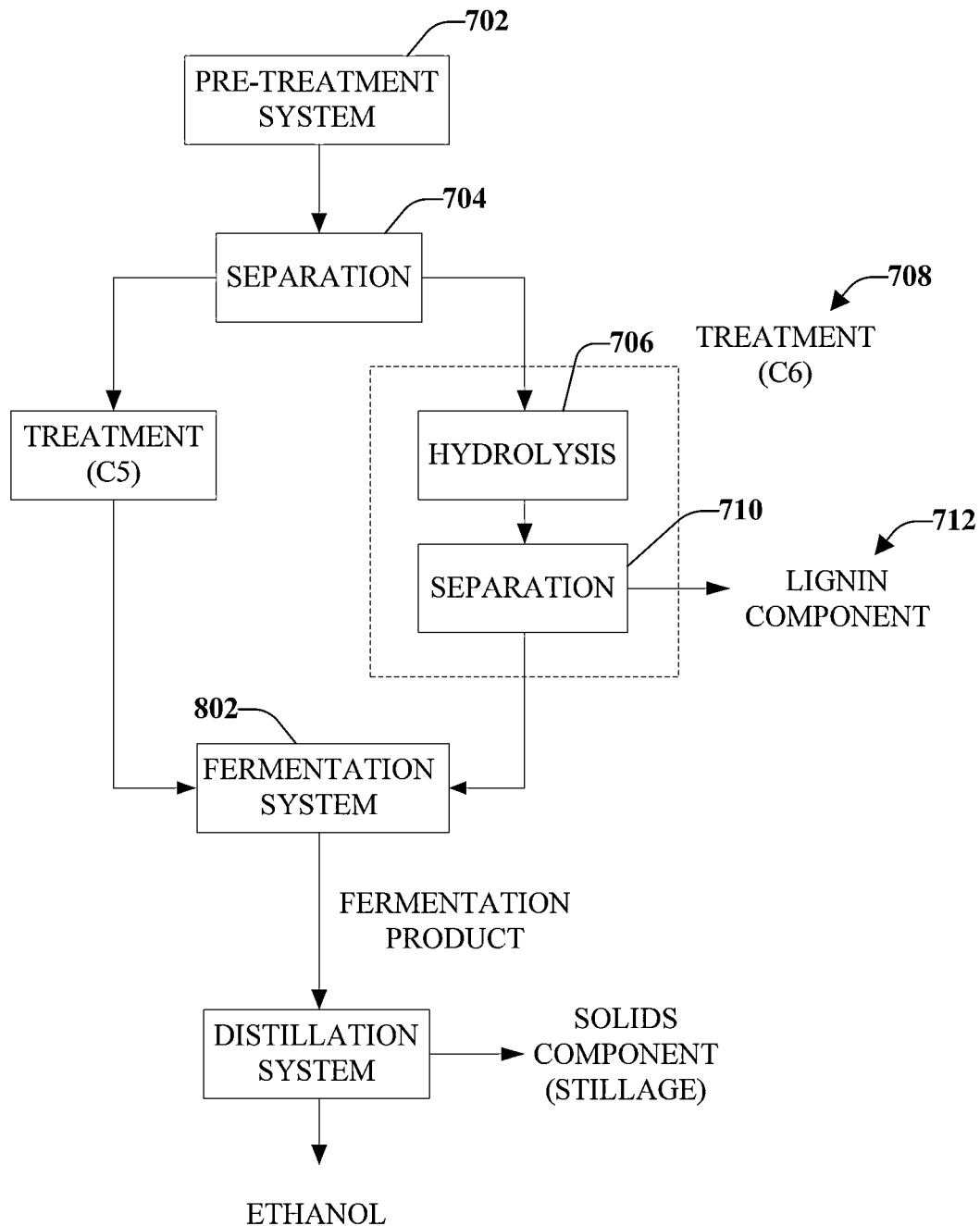
FIGS. 7A, 7B, 8A, and 8B are exemplary embodiments of systems to recover a lignin component.
Figure 7B:
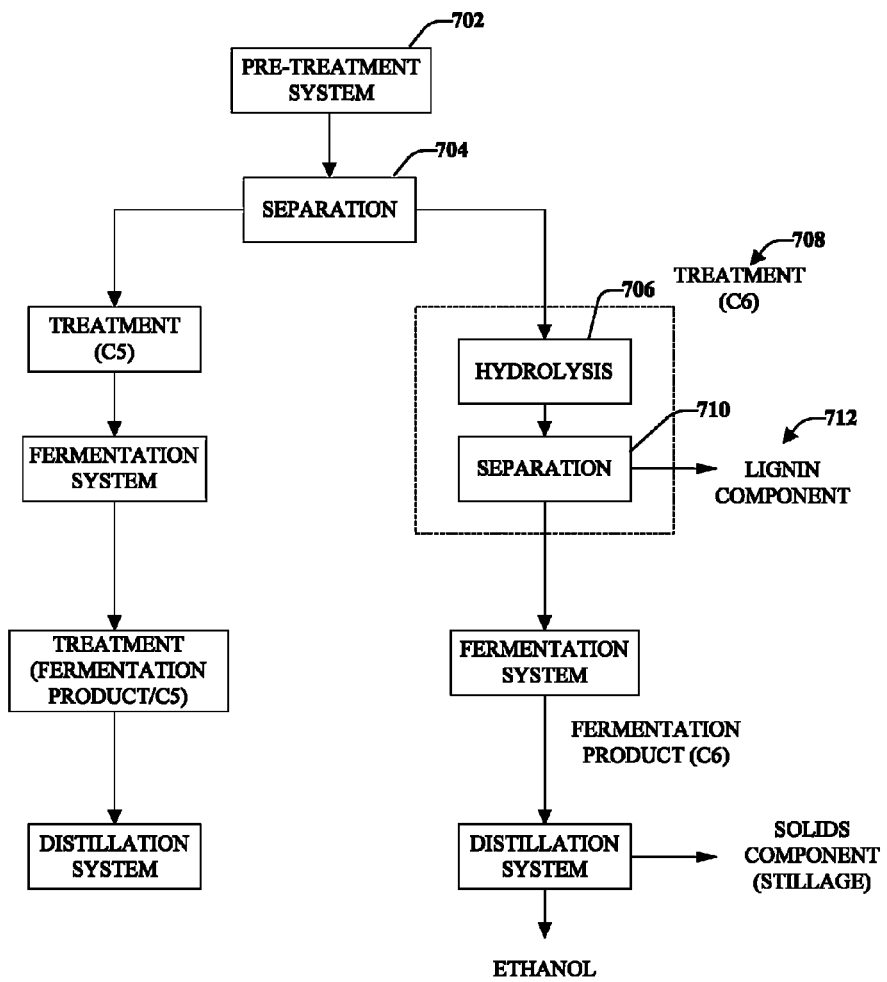

As shown in FIGS. 7A and 7B, the treatment 708 of the solids component (C6) comprises an enzymatic hydrolysis 706 step, and may also comprise separation 710 of a lignin containing solids component (e.g. lignin component 712) from the hydrolysate stream. The separation may be performed using a centrifuge, such as a decanter centrifuge. The hydrolysate stream typically comprises approximately 7 to 10 percent solids, which may comprise about 48 to 62 percent lignin (dry weight). A typical composition of the lignin component separated from hydrolysed solids component (C6) is shown in TABLE 4A. The lignin component separated (e.g. by centrifugation) from the hydrolysate stream may comprise approximately 25 to 35 percent solids.

Figure 8A:
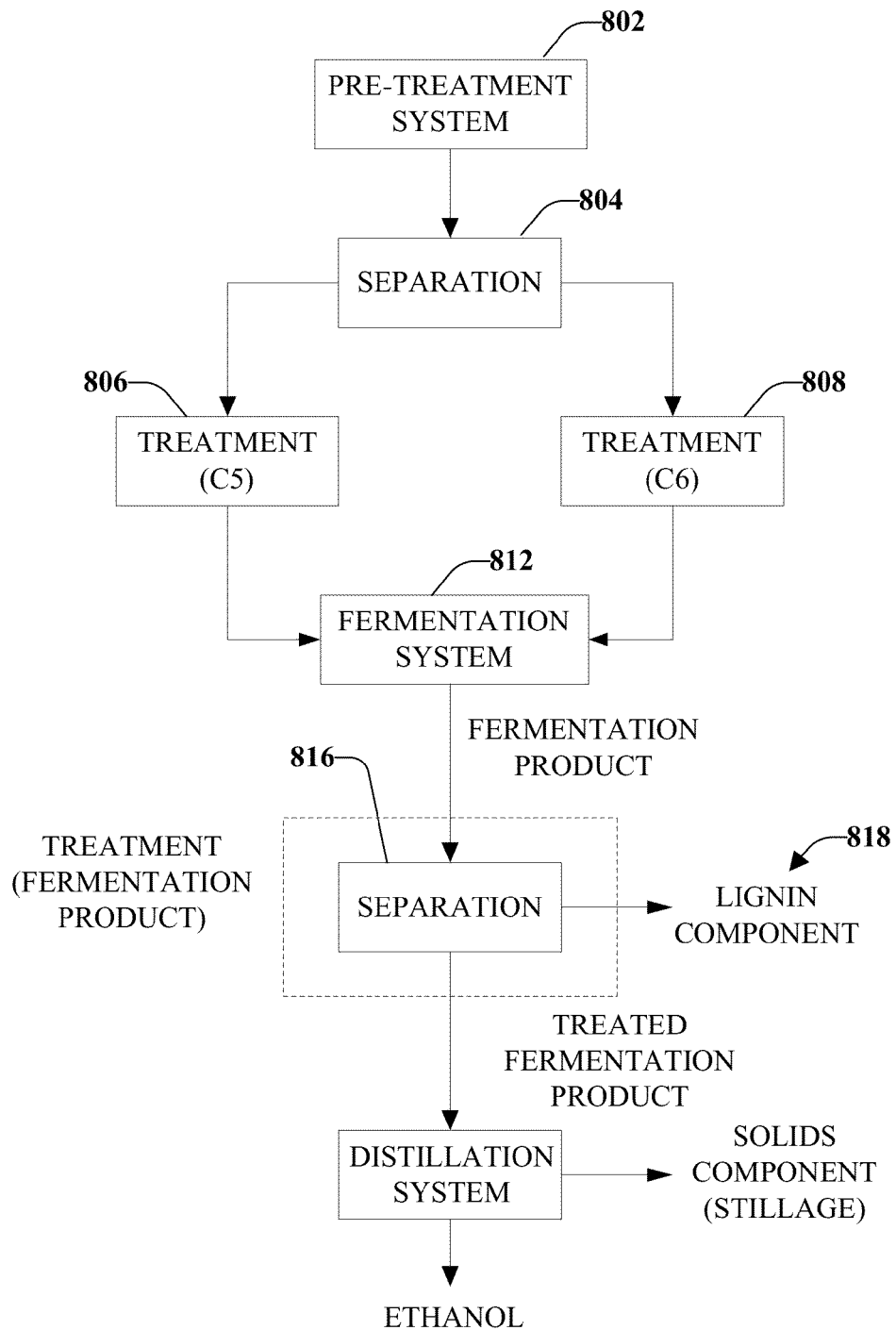
Figure 8B:
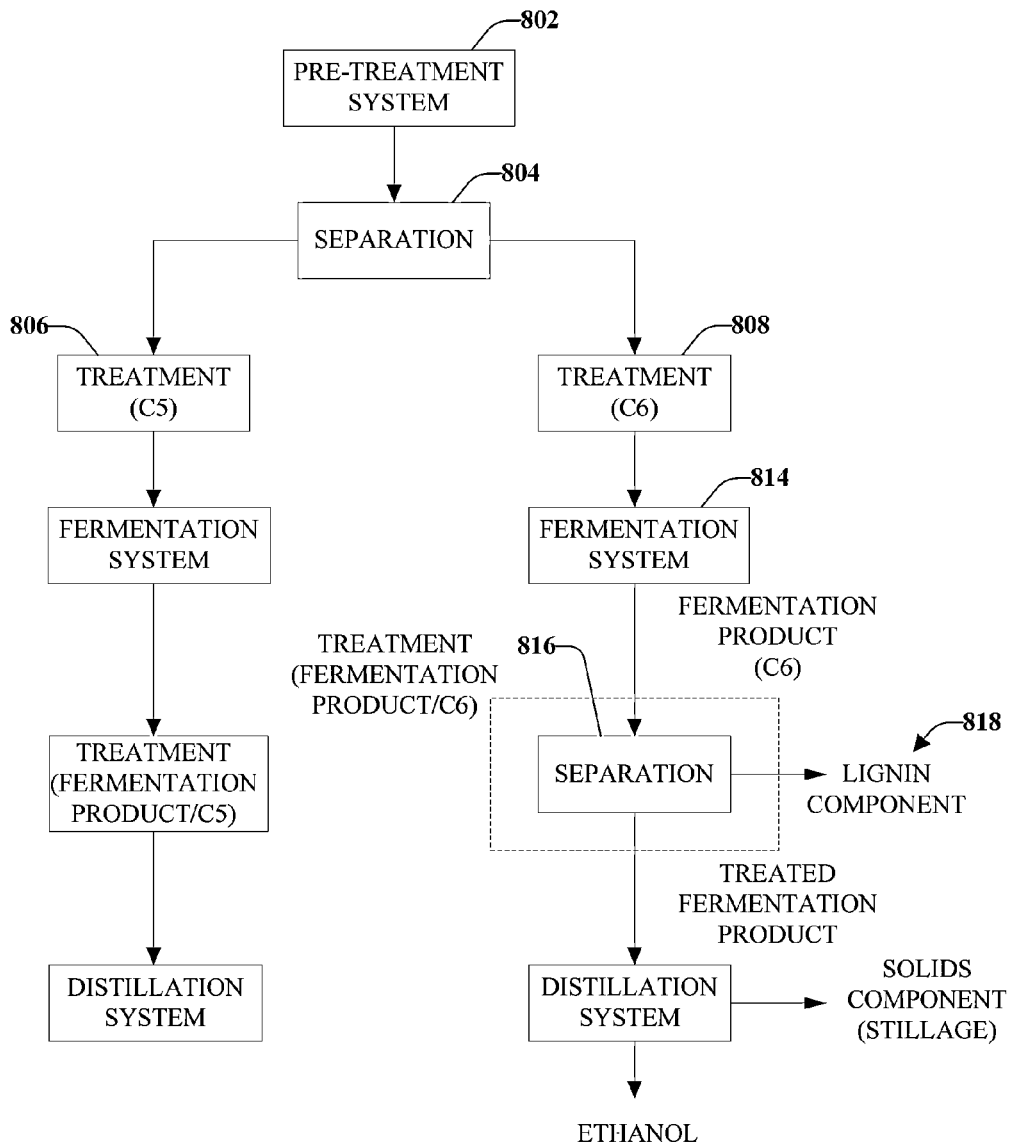

Referring to FIGS. 8A and 8B, a treatment system of the fermentation product is shown. Lignocellulosic biomass is pre-treated in a pre-treatment system 802 to produce pre-treated biomass. The pre-treated biomass is separated in a first separation system 804 into a first liquid component (C5) and a first solids component (C6). The C5 stream and the C6 stream may be treated in separate treatment systems 806, 808. The fermentation product of either co-fermentation 812 of C5 and C6 streams or separate fermentation 814 of the C6 stream can be treated to separate (in a second separation system 816) a lignin containing solids component (e.g. lignin component 818). The second separation may be performed using a centrifuge, such as a decanter centrifuge. The fermentation product typically comprises approximately 8 to 12 percent solids, which may comprise about 57 to 67 percent lignin (dry weight). A typical composition of the lignin component separated (e.g. by centrifugation) from hydrolysed and fermented solids component (C6) (e.g. fermentation product) is shown in TABLE 4B. The lignin component separated from the fermentation product may comprise approximately 25 to 35 percent solids. According to an embodiment, at least a majority of the lignin is not sulfonated.

Lignin is a mixture of aromatic hydrocarbons, and can be used as a feedstock for chemicals or other products (such as adhesives, binders and carbon fibers), blended into polymers, or used for its heat value by combustion. The different applications of lignin would benefit from a product that is manageable in transportation, storage and handling systems. The lignin component as it is recovered from the cellulosic ethanol production process, may be a thick, pasty solution, with a consistency much like crude oil or tomato paste, and a viscosity of potentially over 100,000 centipoise. The lignin component may be dried to enhance its material handling characteristics, or to reduce its moisture content in order to improve combustibility, but drying lignin requires large amounts of energy, and typically produces a powder-like product that may create dust problems.

Pelletizing may be used as a way to improve the handling properties of materials with small particle size or poor flowability. Pellets are easy to handle, store and transport, create fewer problems with dust, and in a combustion system (such as a solid fuel boiler) the pellets also combust well due to lower moisture and increased airflow, as compared to wet materials or materials with small particle size.

Lignin has been used as an additive or a binder in pellets made in extruder type pelletizers at concentrations of about 2 to 10 percent lignin. Extruder type pelletizers, however, are typically used with relatively dry materials (moisture content of about 10 to 20 percent). To use lignin without pre-drying in the form of the lignin component recovered from the cellulosic ethanol production process at a higher exclusion rate (50 percent of lignin or higher) a different type pelletizing system is needed.

Figure 9A:
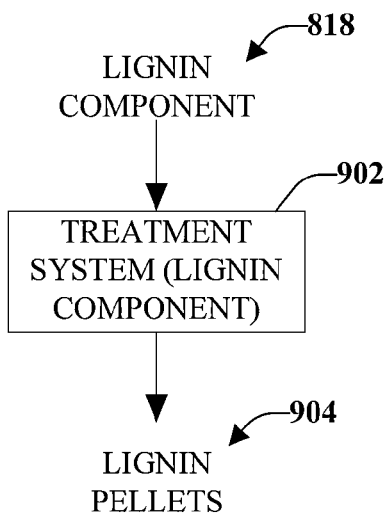
FIGS. 9A and 9B are exemplary embodiments of treatment systems to produce pellets that comprise lignin.
Figure 9B:
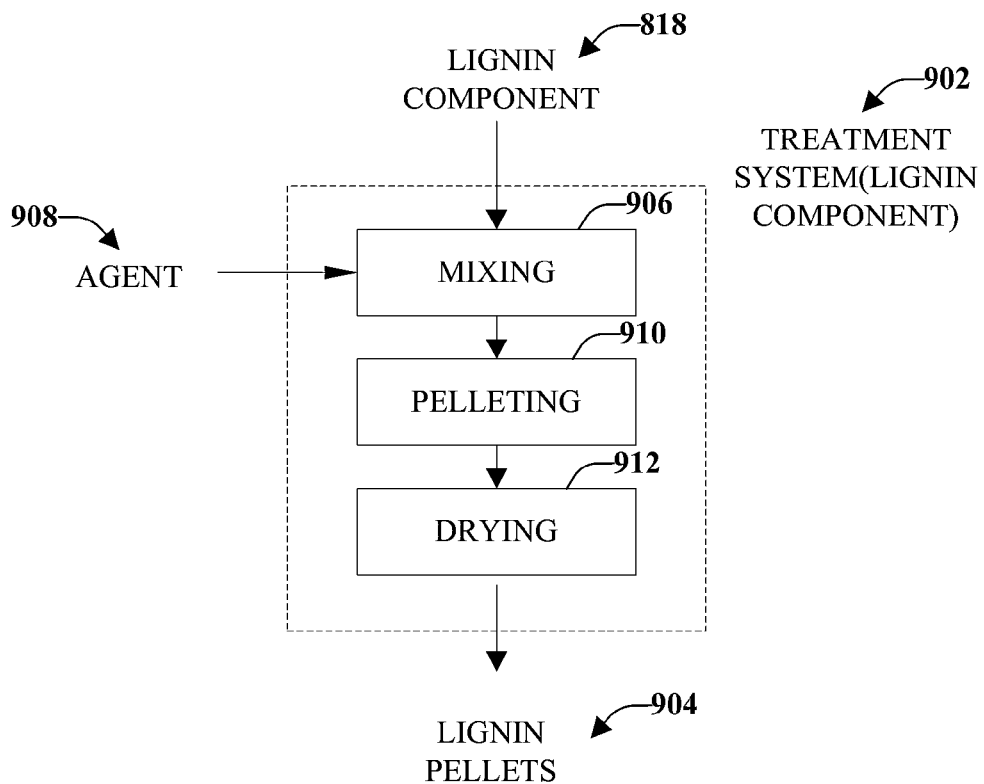

As shown in FIGS. 9A and 9B, according to an embodiment of the current invention, the lignin component 818 may be further treated (in a treatment system 902) to produce pellets 904 that comprise lignin at a concentration of at least 50 percent. Preferably, the pellets comprise at least 65 percent lignin. As shown in FIG. 9B, the treatment system 902 may comprise a mixing step 906, where an agent 908 may optionally be mixed with the lignin component, a pelleting step 910 and optionally a drying step 912. The agent 908 may comprise an additive or a filler that can facilitate pelleting, such as ash, fiber (e.g. corn fiber, oat hulls, etc.), saw dust or dried distillers grains or combinations thereof. The filler may be chosen from available materials so that it also facilitates the further use (e.g. combustion) of the lignin pellets.

Figure 10A:
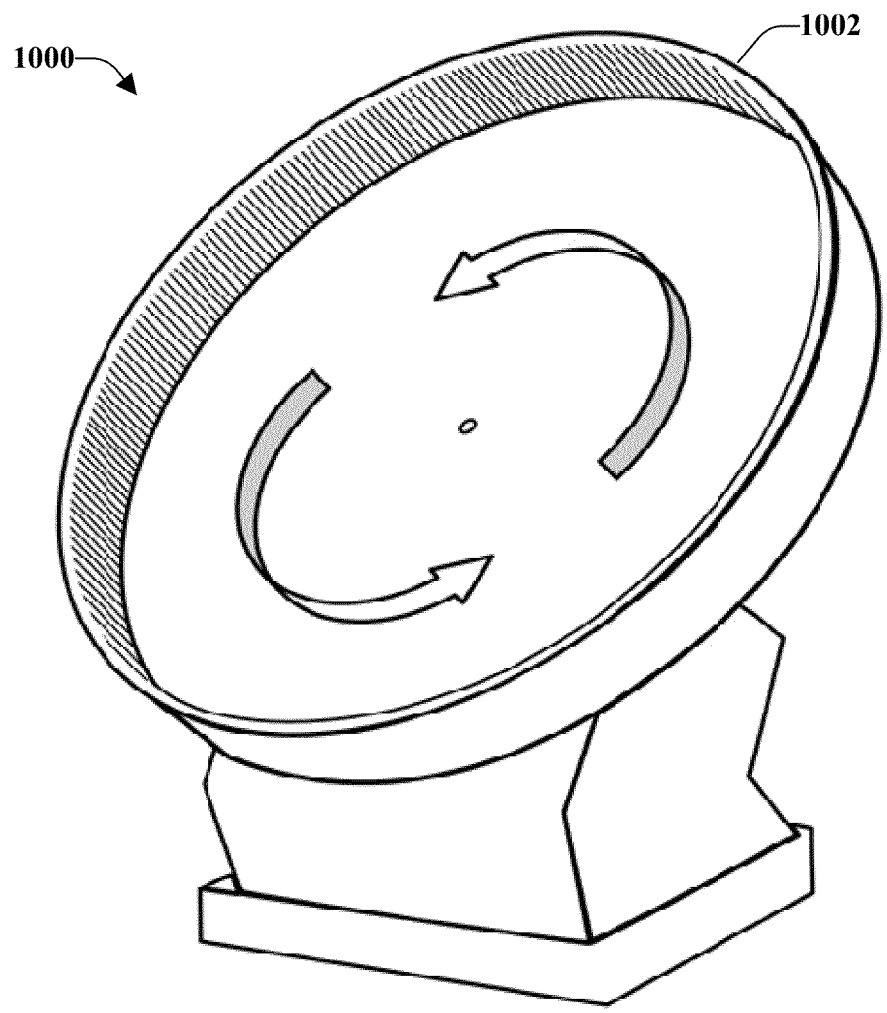
FIGS. 10A and 10B are an exemplary embodiment of a disc pelletizer that may be used to produce pellets from the lignin component, according to an embodiment.
Figure 10B:
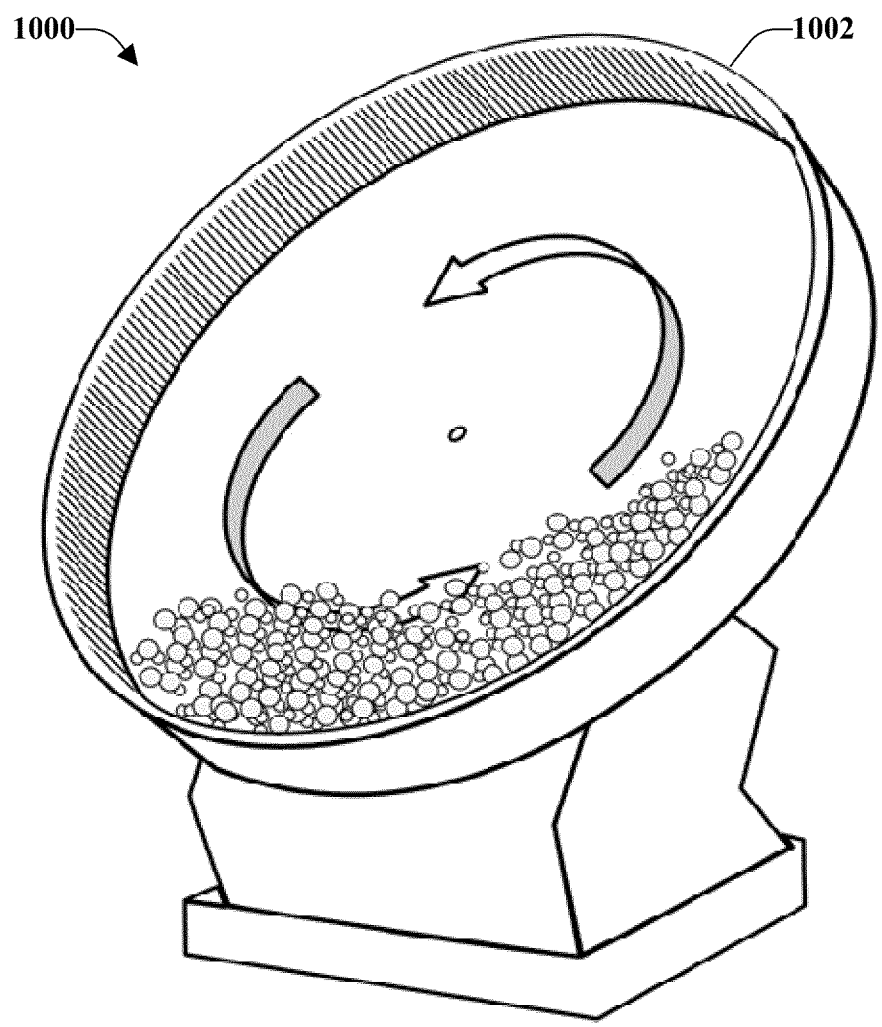

Referring to FIGS. 10A and 10B, a disc pelletizer 1000 may be used to produce pellets from the lignin component, which is high in moisture (e.g. 65 to 75 percent by weight). A disc pelletizer 1000 comprises a rotating pan 1002 positioned at an angle. Material is supplied onto the pan and the rotating motion allows the material to "roll back" on itself creating clusters of material, which with further processing form pellets. The pan may be heated or warmed to facilitate drying of the product and to aid the pellet forming process.

The pellets may be dried to a desired moisture content (e.g. approximately 8 to 20 percent moisture) using a dryer. According to a preferred embodiment, the pellets are dried in an air flow (e.g. in a forced air dryer) to a desired moisture content. According to a most preferred embodiment, the pellets are dried at an ambient temperature (e.g. about 18 to 25 degrees Celsius) air flow to a desired moisture content.

The lignin component may be subjected to a treatment to increase the lignin concentration prior to pelletizing, if a high concentration lignin (e.g. 90 percent or more) pellet is desired, for example for use in a polymer application or a carbon fiber application. A treatment system may be used as described in U.S. application Ser. No. 12/827,948 entitled "SYSTEM FOR RECOVERY OF LIGNIN FROM BIOMASS", which is incorporated by reference in its entirety.

A series of examples was conducted according to an exemplary embodiment of the system (as shown in FIGS. 9B and 10B) in an effort to determine suitable operating conditions for the production of lignin pellets. Data from the examples is shown in TABLE 5.

Example 1

The treatment system (as shown in FIG. 9B) was used in Example 1 to determine a suitable moisture contents of the lignin component for producing pellets. Samples were prepared from pre-treated and hydrolysed corn cobs by separating the lignin component by centrifugation. The sample comprised approximately 40 percent solids or 60 percent moisture, and about 60 percent lignin by dry weight. Part of the sample was dried in a forced air oven to a powder with a moisture content of approximately 37 percent. Dried lignin component was mixed with the wet lignin component to create samples with different moisture contents. The samples were supplied to a rotating drum pelletizer and the samples were monitored for pellet formation. It was observed that the sample with 60 percent moisture was too wet for pelleting and the sample with 37 percent moisture was too dry for pelleting; in either case, no pellets were formed. It was also observed that the sample with a moisture content of about 46 percent did not form pellets well, but that the sample with about 55 percent moisture formed pellets very well.

Example 2

The treatment system (as shown in FIG. 9B) was used in Example 2 to test suitable drying conditions for pellets that were produced as described Example 1 using lignin component with about 55 percent moisture. The samples were dried in ambient air, in ambient forced air or by flash drying, or a combination thereof, as shown in TABLE 5. A rotating pan with an electrical heating element positioned above was used for flash drying. The drying time was monitored and the samples were tested for moisture after drying. The results of the experiment are shown in TABLE 5. It was observed that a moisture content of 10 percent could be reached in ambient conditions in about 20 hours (overnight drying), or a moisture content of 17 percent could be reached in forced air ambient conditions in 3 hours. It was also observed that flash drying the pellets prior to ambient air drying did not improve the results significantly, and that flash drying alone for 12 minutes did not dry the pellets effectively.

The embodiments as disclosed and described in the application (including the FIGURES and Examples) are intended to be illustrative and explanatory of the present invention. Modifications and variations of the disclosed embodiments, for example, of the apparatus and processes employed (or to be employed) as well as of the compositions and treatments used (or to be used), are possible; all such modifications and variations are intended to be within the scope of the present invention.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

What is claimed is:

1. Pellets comprising lignin, wherein the pellets comprise at least 50 percent lignin by dry weight and from 40 to 75 weight percent moisture.

2. The pellets of claim 1, wherein the pellets comprise at least 65 percent lignin by dry weight.

3. The pellets of claim 1, wherein the pellets comprise at least 80 percent lignin by dry weight.

4. The pellets of claim 1, wherein the pellets comprise at least 90 percent lignin by dry weight.

5. The pellets of claim 1, wherein the pellets comprise at least 95 percent lignin by dry weight.

6. The pellets of claim 1, wherein the lignin is recovered from lignocellulosic biomass comprising at least one of corn cobs, corn plant husks, corn plant leaves, corn plant stalks, or combinations thereof.

7. The method of claim 6 wherein the lignocellulosic biomass consists essentially of corn cobs, corn plant husks, corn plant leaves, corn stalks, or combinations thereof.

8. The pellets of claim 1, wherein the pellets comprise an agent selected from the group consisting of ash, fiber, saw dust, distillers dried grains, or combinations thereof.

9. The pellets of claim 8, wherein the agent comprises no more than 50 percent of the pellets by dry weight.

10. The pellets of claim 1, wherein at least a majority of the lignin is not sulfonated.

11. Pellets produced from a lignin composition by a process comprising:
pre-treating lignocellulosic biomass into pre-treated biomass;
separating the pre-treated biomass into a first liquid component comprising sugars and a first solids component comprising cellulose and the lignin composition;
hydrolysing the first solids component of the pre-treated biomass into a hydrolysed biomass comprising sugars and the lignin composition;
separating the hydrolysed biomass into a second liquid component comprising sugars and a second solids component comprising the lignin composition;
supplying the second solids component comprising the lignin composition to a pelleting apparatus to produce the pellets;
wherein the lignocellulosic biomass comprises cellulose, hemi-cellulose and lignin, and
wherein the pellets comprise at least 50 percent lignin by dry weight and from 40 to 75 weight percent moisture.

12. The pellets of claim 11, wherein the supplying comprises supplying the second solids component to a pelleting apparatus comprising a disk pelletizer.

13. The pellets of claim 11, wherein the process further comprises:
supplying the second solids component to a fermentation system to produce fermentation product;

separating the fermentation product to a third liquid component and a third solids component comprising the lignin composition; and supplying the third solids component to the pelleting apparatus to produce the pellets.

14. The pellets of claim 11, wherein the pellets comprise at least 65 percent lignin by dry weight.

15. The pellets of claim 11, wherein the process further comprises supplying the second solids component to a treatment system to increase the concentration of lignin in the lignin composition.

16. The pellets of claim 15, wherein the pellets comprise at least 80 percent lignin by dry weight.

17. The pellets of claim 15, wherein the pellets comprise at least 90 percent lignin by dry weight.

18. The pellets of claim 15, wherein the pellets comprise at least 95 percent lignin by dry weight.

19. The pellets of claim 11, wherein the process further comprises drying the pellets.

20. The pellets of claim 11, wherein the lignocellulosic biomass comprises at least one of corn cobs, corn plant husks, corn plant leaves, corn plant stalks, or combinations thereof.

21. The pellets of claim 11, wherein the lignocellulosic biomass consists essentially of corn cobs, corn plant husks, corn plant leaves, corn stalks, or combinations thereof.

22. The pellets of claim 11, wherein at least a portion of the lignin is not sulfonated.

23. The pellets of claim 1, comprising from about 57-67 percent lignin and from about 2 to 22 weight percent ash based on total solids.

24. The pellets of claim 1, comprising from about 57-67 percent lignin, from about 5.5 to 7.5 percent cellulose, and from about 1.8 to 3.9 percent hemicellulose based on total solids.

25. The pellets of claim 1, comprising from 40 to 65 percent moisture.

26. The pellets of claim 1, comprising from 45 to 55 percent moisture.

27. Pellets comprising lignin, wherein the pellets comprise from about 57-67 percent lignin, and from about 2 to 22 weight percent ash based on total solids.

28. Pellets comprising lignin, wherein the pellets comprise from about 57-67 percent lignin, from about 5.5 to 7.5 percent cellulose, and from about 1.8 to 3.9 percent hemicellulose based on total solids.

* * * * *